(12) United States Patent
Delcore (10) Patent No.: US 11,786,231 B2
(45) Date of Patent: Oct. 17, 2023

(54) SURGICAL RETRACTOR

(71) Applicant: SECTSEE Surgical Retractors, LLC, Cedar City, UT (US)

(72) Inventor: Randy Delcore, Cedar City, UT (US)

(73) Assignee: SECTSEE Surgical Retractors, LLC, Cedar City, UT (US)

( * ) Notice: Subject to any disclaimer, the term of this patent is extended or adjusted under 35 U.S.C. 154(b) by 0 days.

(21) Appl. No.: 16/817,220

(22) Filed: Mar. 12, 2020

(65) Prior Publication Data

US 2020/0289104 A1    Sep. 17, 2020

Related U.S. Application Data

(60) Provisional application No. 62/817,357, filed on Mar. 12, 2019.

(51) Int. Cl.
*A61B 17/02* (2006.01)
*A61B 17/00* (2006.01)

(52) U.S. Cl.
CPC .... *A61B 17/02* (2013.01); *A61B 2017/00424* (2013.01)

(58) Field of Classification Search
CPC . A61B 17/02; A61B 17/0206; A61B 17/0218; A61B 17/0281

USPC .......................................................... 600/226
See application file for complete search history.

(56) References Cited

U.S. PATENT DOCUMENTS

| | | | | |
|---|---|---|---|---|
| 659,182 A | * | 10/1900 | Pilling | A61B 17/02 600/226 |
| 2005/0085723 A1 | * | 4/2005 | Huebner | A61B 90/39 600/431 |
| 2021/0145428 A1 | * | 5/2021 | Zheng | A61B 17/02 |

* cited by examiner

*Primary Examiner* — Si Ming Ku
(74) *Attorney, Agent, or Firm* — MASCHOFF BRENNAN (57) ABSTRACT

Surgical retractors are disclosed herein. More particularly but not exclusively, in one form, a surgical retractor includes blade portions positioned on opposite ends thereof. The retractor also includes one or more portions positioned between the blade portions which provide an ergonomic handle design configured to facilitate engagement thereof by a user. By way of non-limiting example, in one form the ergonomic design includes a pair of concave surfaces spaced apart and positioned on opposite sides of the body of the retractor from one another. Other features and aspects relating to this and other surgical retractors are disclosed herein.

31 Claims, 6 Drawing Sheets

SURGICAL RETRACTOR

CROSS-REFERENCE TO RELATED APPLICATIONS

This application claims the benefit of U.S. Provisional Patent Application No. 62/817,357 filed Mar. 12, 2020, the content of which is incorporated herein by reference in its entirety.

BACKGROUND

The present disclosure generally relates to surgical retractors, and more particularly but not exclusively, to a surgical retractor that includes blade portions positioned on opposite ends thereof and one or more portions positioned between the blade portions which provide an ergonomic handle design configured to facilitate engagement thereof by a user.

Retractors have been commonly used in surgical procedures to provide necessary access to surgical sites by moving, for example, tissue and other anatomical features surrounding a surgical site. During a surgical procedure, it may be desirable to use a retractor to perform multiple different steps which may, for example, require user manipulation of the retractor between different positions depending on the step being performed. During such manipulation, the retractor may be subject to mishandling by the user resulting in failure to complete a particular step and/or unnecessary trauma to the surgical site or areas surrounding the surgical site.

In view of the foregoing, there remains a need for further contributions in this area of technology.

The claimed subject matter is not limited to embodiments that solve any disadvantages or that operate only in environments such as those described above. Rather, this background is only provided to illustrate examples of where the present disclosure may be utilized.

BRIEF SUMMARY

The present disclosure generally relates to surgical retractors, and more particularly but not exclusively, to a surgical retractor that includes blade portions positioned on opposite ends thereof and one or more portions positioned between the blade portions which provide an ergonomic handle design configured to facilitate engagement thereof by a user.

In one embodiment, a surgical retractor includes an elongate body extending along a longitudinal axis between a proximal end having a proximal blade portion extending transversely to the longitudinal axis and an opposite distal end having a distal blade portion extending transversely to the longitudinal axis. The elongate body includes a first portion positioned between the proximal end and the distal end having an enlarged lateral width, and a second portion positioned between the first portion and the distal end having an enlarged lateral width. The first portion includes a concave surface positioned on a first side of the longitudinal axis, and the second portion includes a concave surface positioned on an opposite, second side of the longitudinal axis. In one aspect, the distal blade portion extends from the longitudinal axis in a direction opposite of the direction from which the proximal blade portion extends from the longitudinal axis. In this or another aspect, each of the concave surfaces is positioned on an opposite side of the longitudinal axis relative to the respective blade portion positioned closest to it.

In another embodiment, a surgical retractor includes an elongate body extending along a longitudinal axis between a proximal end and an opposite distal end. A proximal blade portion extends transversely to the longitudinal axis from the proximal end, and a distal blade portion extends transversely to the longitudinal axis from the distal end. The elongate body includes a first arcuate surface positioned on an opposite side of the longitudinal axis from the proximal blade portion, and a second arcuate surface positioned between the first arcuate surface and the distal end and on an opposite side of the longitudinal axis from the first arcuate surface and the distal blade portion.

In alternative embodiments, assemblies, systems, apparatuses, devices and methods relating to surgical retractors are provided.

This Summary is provided to introduce a selection of concepts in a simplified form that are further described below in the Detailed Description. This Summary is not intended to identify key features or essential characteristics of the disclosed subject matter, nor is it intended to be used as an aid in determining the scope of the disclosed subject matter.

Additional features and advantages will be set forth in the description which follows, and in part will be obvious from the description, or may be learned by the practice of the invention. The features and advantages may be realized and obtained by means of the instruments and combinations particularly pointed out in the appended claims. These and other features of the present invention will become more fully apparent from the following description and appended claims, or may be learned by the practice of the invention as set forth hereinafter.

DETAILED DESCRIPTION

For purposes of promoting an understanding of the present disclosure, reference will now be made to the following embodiments and specific language will be used to describe the same. It will nevertheless be understood that no limitation of the scope of the disclosure is thereby intended, such alterations and further modifications in the described subject matter, and such further applications of the disclosed principles as described herein being contemplated as would normally occur to one skilled in the art to which the disclosure relates.

The terms and words used in the following description and claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

The present disclosure generally relates to surgical retractors, and more particularly but not exclusively, to a surgical retractor that includes blade portions positioned on opposite ends thereof and one or more portions positioned between the blade portions which provide an ergonomic handle design configured to facilitate engagement thereof by a user.

Figure 3:
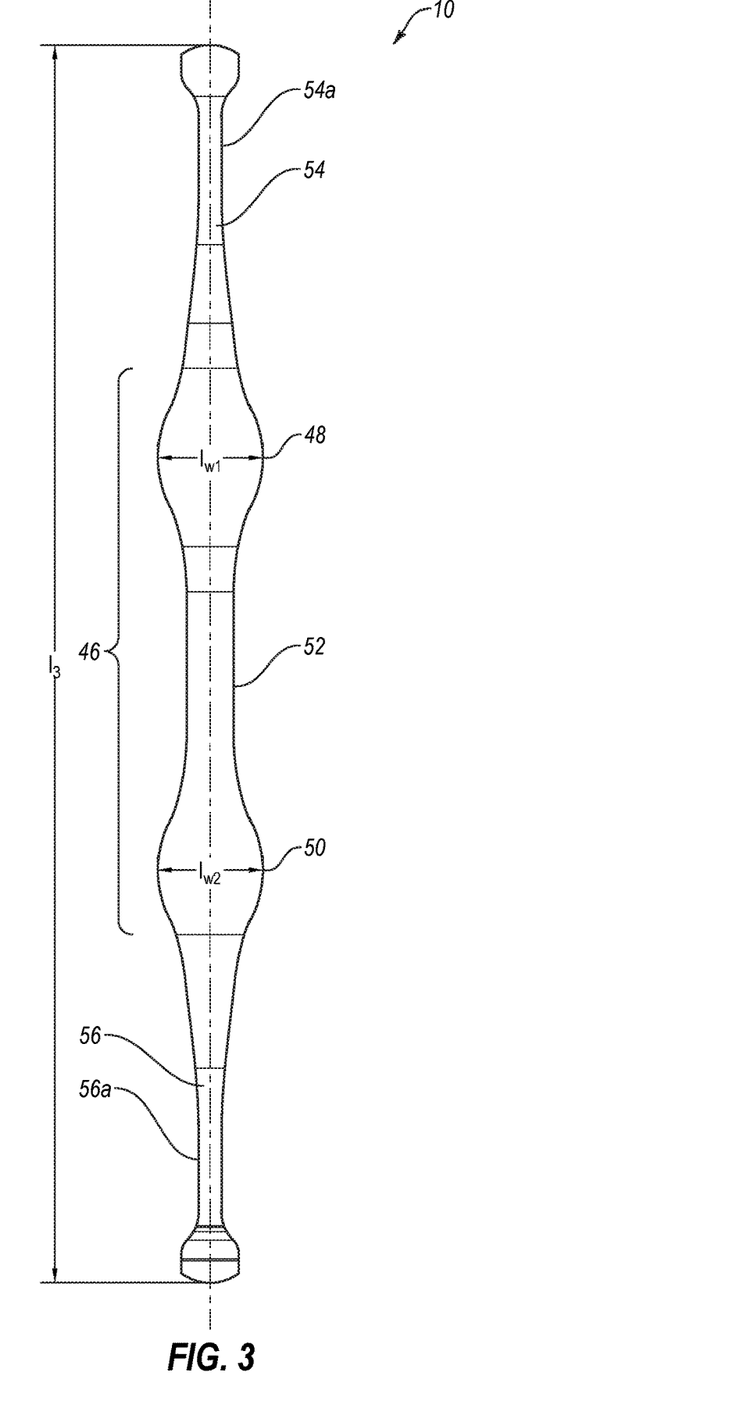
FIG. 3 is a front plan view of the surgical retractor of FIG. 1.
Figure 4:
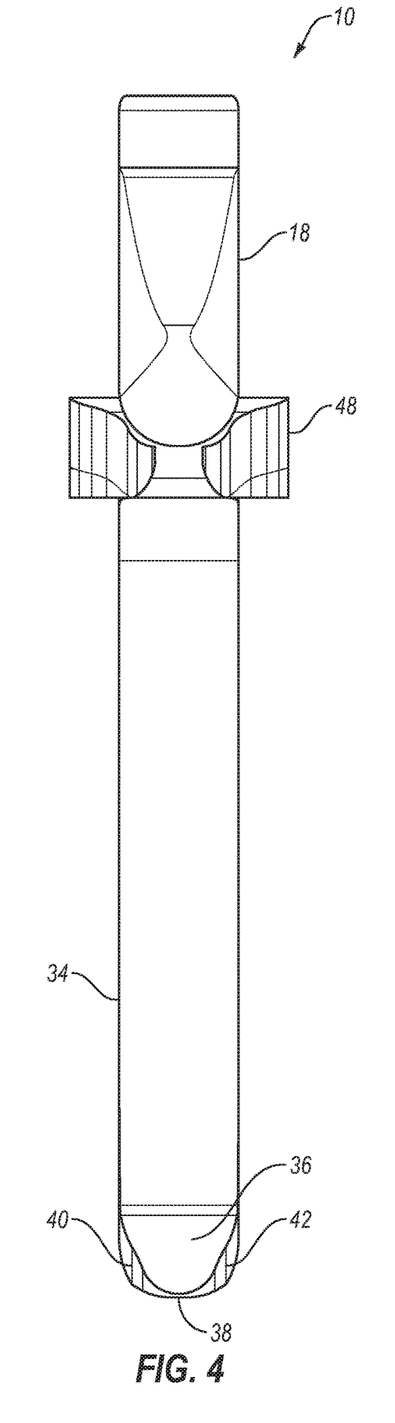
FIG. 4 is a proximal end view of the surgical retractor of FIG. 1.
Figure 5:
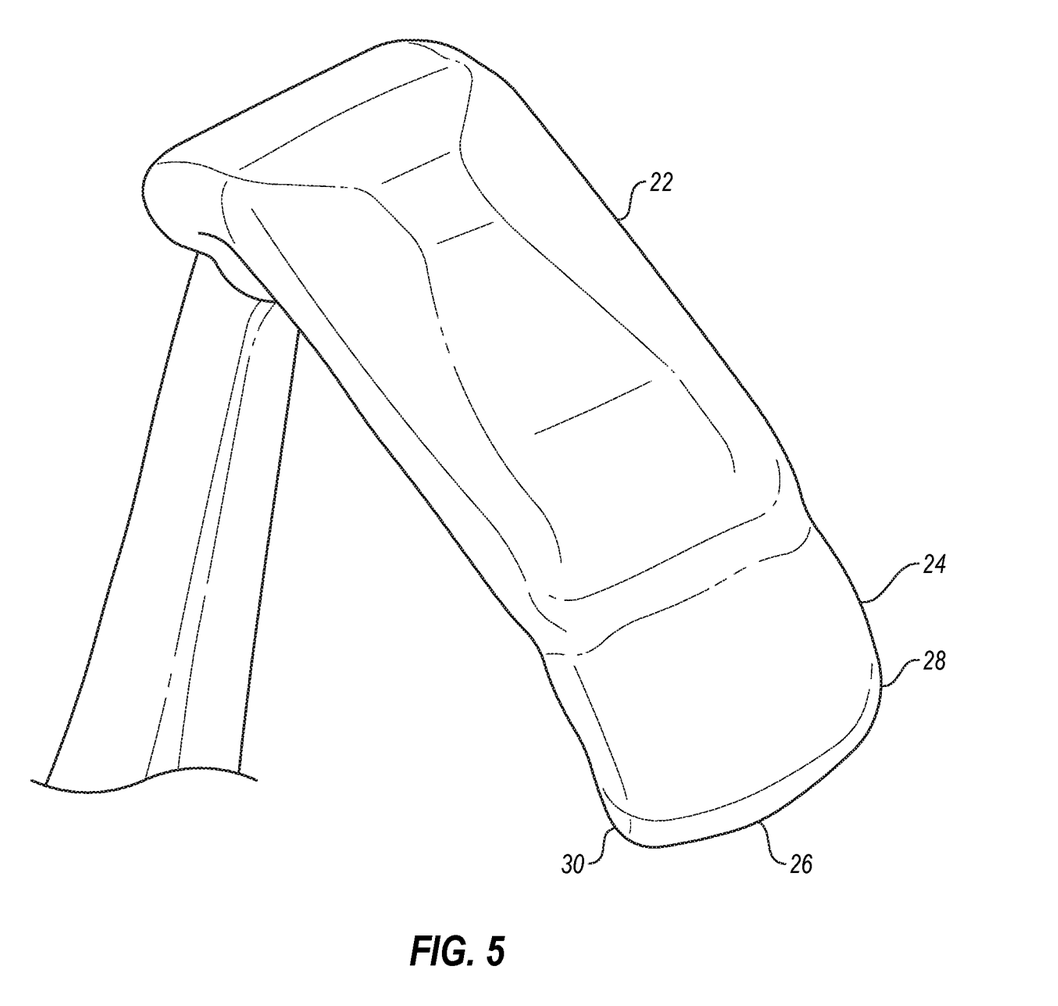
FIG. 5 is an enlarged, perspective view of the proximal end of the surgical retractor of FIG. 1.

Turning now generally to FIGS. 1-5, there is illustrated a surgical retractor 10 which includes an elongate body 12 which generally extends along a longitudinal axis L between a proximal end 14 and an opposite distal end 16. Retractor 10 also includes a proximal blade portion 18 and a distal blade portion 20. Proximal blade portion 18 includes a main body 22 which extends transversely to longitudinal axis L in a first direction from proximal end 14 of elongate body 12. Proximal blade portion 18 also includes an end portion 24 which extends transversely to main body 22 and terminates at proximal tip 26. As best seen in FIG. 5 for example, end portion 24 of proximal blade portion 18 generally has the same width as main body 22. However, forms in which all or part of end portion 24 tapers toward proximal tip 26 such that at least a portion of end portion 24 has a reduced width relative to main body 22 are possible. Adjacent to proximal tip 26, end portion 24 includes rounded portions 28, 30, although forms where this portion of end portion 24 is linear are also possible. In the illustrated form for example, end portion 24 also has a reduced thickness relative to main body 22 which, in turn, has a reduced thickness relative to the portion of elongate body 12 from which it extends. However, forms in which the thickness of these elements is different from the illustrated form are contemplated.

Figure 1:
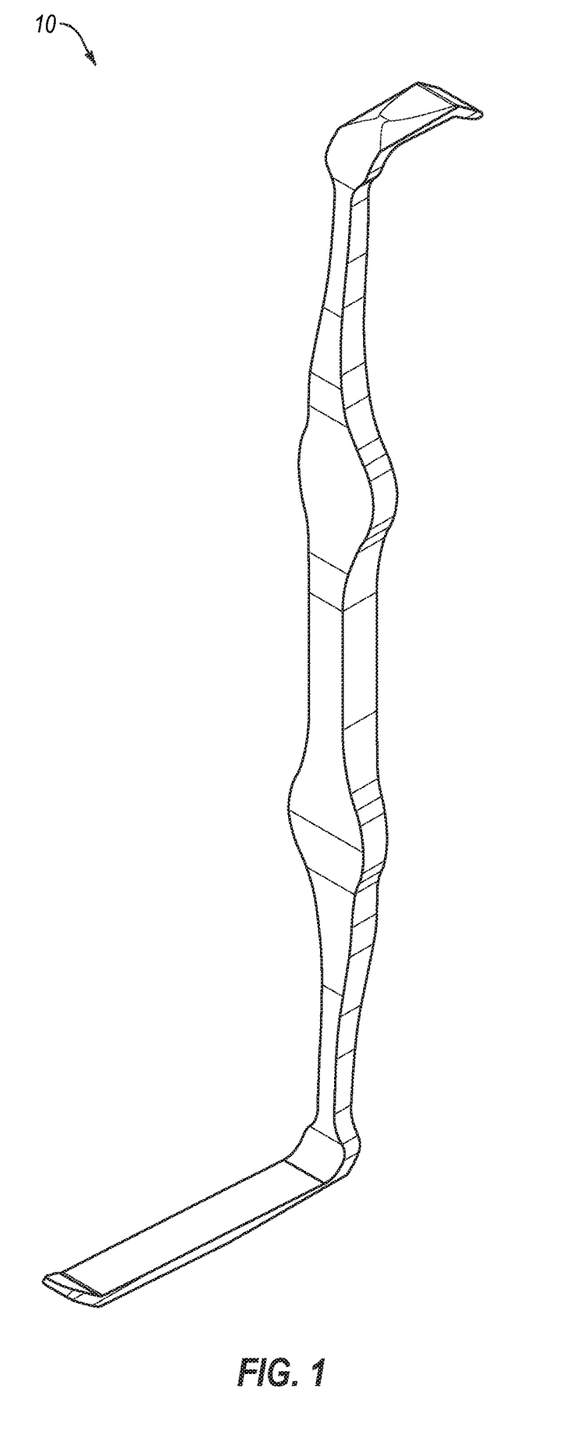
FIG. 1 is a perspective view of a surgical retractor.
Figure 2:
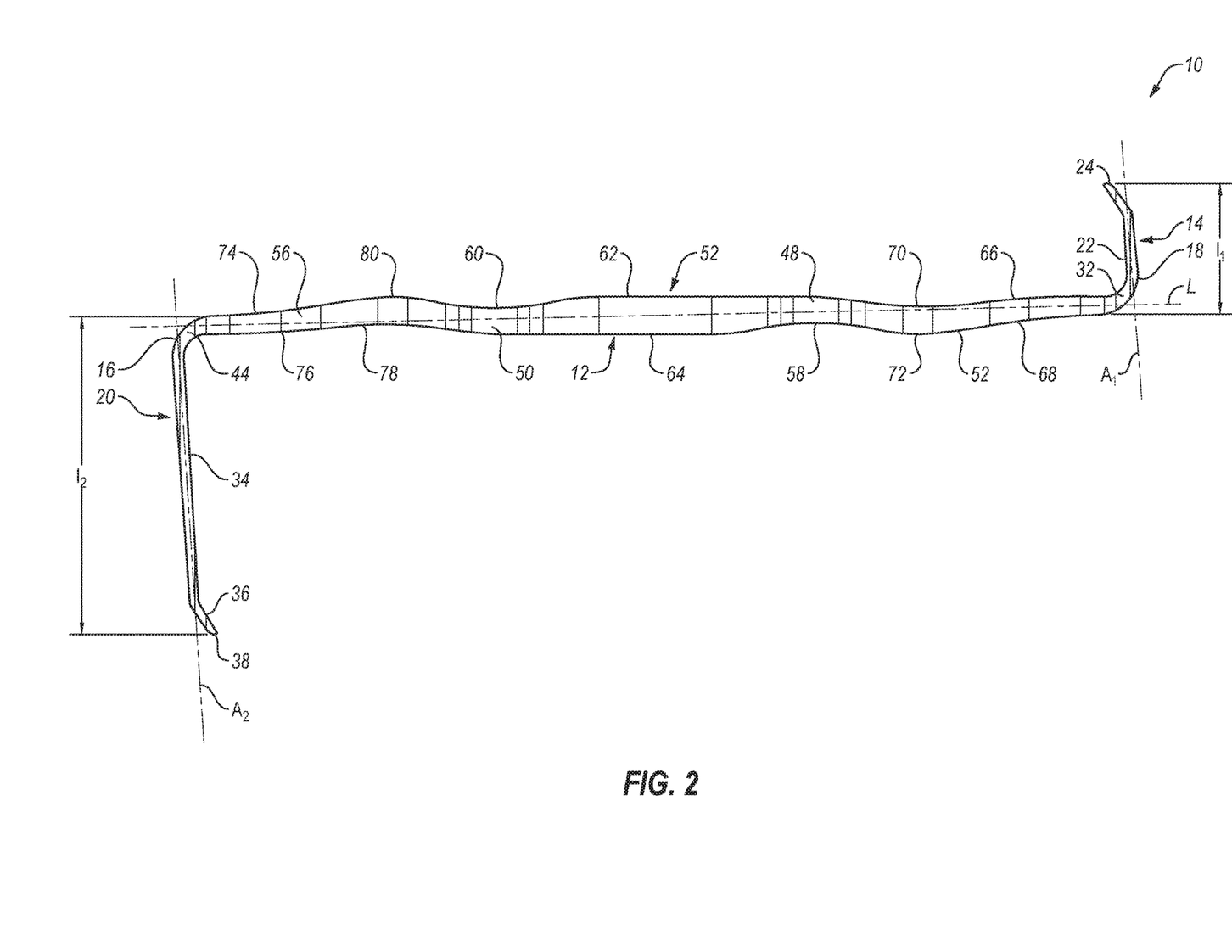
FIG. 2 is a side view of the surgical retractor of FIG. 1.

As best seen in FIG. 2 for example, main body 22 of proximal blade portion 18 extends from elongate body 12 along rounded transition 32 which has a curvilinear configuration. In one or more non-illustrated forms, all or part of transition 32 may have a non-curvilinear configuration however. In the illustrated form, main body 22 of proximal blade portion 18 extends at an oblique angle toward distal end 16 relative to longitudinal axis L However, in other non-illustrated forms, it is contemplated that main body portion 22 of proximal blade portion 18 may extend orthogonally to longitudinal axis L. Without being limited to any particular form, it is contemplated that proximal blade portion 18 may include a length $l_1$ in the range of 10 mm to 30 mm. In another form, length $l_1$ may be in the range of 14 mm to 26 mm. In yet another form, length $l_1$ may be in the range of 16 mm to 22 mm.

As indicated above, surgical retractor 10 also includes a distal blade portion 20 positioned opposite of proximal blade portion 18. Distal blade portion 20 includes a main body 34 which extends transversely to longitudinal axis L on an opposite, second direction relative to proximal blade portion 20 from distal end 16 of elongate body 12. Distal blade portion 20 also includes an end portion 36 which extends transversely to main body 34 and terminates at a distal tip 38. As best seen in FIG. 4 for example, the width of end portion 36 of distal blade portion 20 tapers along chamfered portions 40, 42 to distal tip 38 such that end portion 36 has a reduced width relative to main body 34. However, forms in which all or part of end portion 36 has the same width as main body 34 are possible. In the illustrated form for example, end portion 36 has a reduced thickness relative to main body 34 which, in turn, has a reduced thickness relative to the portion of elongate body 12 from which it extends. However, forms in which the thickness of these elements is different from the illustrated form are contemplated.

As best seen in FIG. 2 for example, main body 34 of distal blade portion 20 extends from elongate body 12 along rounded transition 44 which has a curvilinear configuration. In one or more non-illustrated forms, all or part of transition 44 may have a non-curvilinear configuration however. In the illustrated form, main body 34 of distal blade portion 20 extends at an oblique angle toward proximal end 14 relative to longitudinal axis L. However, forms in which main body 34 of distal blade portion 34 extends orthogonally to longitudinal axis L are also possible. Since, as indicated above, main body 22 of proximal blade portion 18 extends at an oblique angle toward distal end 16 relative to longitudinal axis L, it should be appreciated that main body 22 of proximal blade portion 18 extends transversely to main body 34 of distal blade portion. Similarly, it should be understood that axis $A_1$ along which main body 22 extends and axis $A_2$ along which main body 34 extends cross one another at an intersection (not shown). While both main body 22 and main body 34 extend obliquely to longitudinal axis L in the illustrated form, it should be appreciated that forms in which one of main body 22 and main body 34 extends obliquely to longitudinal axis L and the other extends orthogonally to longitudinal axis L are contemplated and would still result in a transverse relationship between one another.

Without being limited to any particular form, it is contemplated that distal blade portion 20 may include a length $l_2$ in the range of 30 mm to 60 mm. In another form, length $l_2$ may be in the range of 35 mm to 50 mm. In yet another form, length $l_2$ may be in the range of 40 mm to 46 mm. In one form for example, surgical retractor 10 includes a length ratio between $l_2$ and $l_1$ in the range of about 3:1 to about 1.8:1. In another form, the length ratio between $l_2$ and $l_1$ may be in the range of about 2.5:1 to about 1.9:1. In yet another form, the length ratio between $l_2$ and $l_1$ may be in the range of about 2.5:1 to about 2.1:1. In addition, without being limited to any particular form, surgical retractor 10 may include a length ratio between length $l_2$ and an overall length $l_3$ (FIG. 3) in the range of about 1:4 to 1:2. In another form, the length ratio between length $l_2$ and an overall length $l_3$ (FIG. 3) may be about 1:3. It should be appreciated that the lengths and ratios described herein are exemplary and non-limiting, and that alternative lengths and ratios are contemplated.

Positioned between proximal blade portion 18 and distal blade portion 20, elongate body 12 of surgical retractor 10 includes a handle portion 46 configured to facilitate use and handling of surgical retractor 10, although use and manipulation of surgical retractor 10 through engagement of other portions thereof are also possible. Handle portion 46 includes a proximal grip 48, a distal grip 50, and an intermediate connecting portion 52 positioned between and spacing apart proximal grip 48 and distal grip 50. A proximal connecting portion or neck 54 extends from proximal grip 48 to proximal end 14 and spaces proximal grip 48 from proximal end 14, and a distal connecting portion or neck 56 extends from distal grip 50 to distal end 16 and spaces distal grip 50 from distal end 16.

As best illustrated in FIG. 2 for example, proximal grip 48 includes a concave surface 58 positioned on a first side of longitudinal axis L and distal grip 50 includes a concave surface 60 positioned on an opposite, second side of longitudinal axis L. Concave surface 58 of proximal grip 48 is also positioned on an opposite side of longitudinal axis L from proximal blade portion 18 and concave surface 60 is positioned on an opposite side of longitudinal axis L from distal blade portion 20. With particular reference to FIG. 3 for example, proximal grip 48 includes an enlarged lateral width $lw_1$ relative to proximal neck 54 and intermediate connecting portion 52, and distal grip 50 includes an enlarged lateral width $lw_2$ relative to distal neck 56 and intermediate connecting portion 52. In this arrangement, the enlarged width of proximal grip 48 extends in a plane which is orthogonal to the plane of the concavity of concave surface 58, and the enlarged width of distal grip 50 extends in a plane which is orthogonal to the plane of the concavity of concave surface 60. More specifically, each of proximal grip 48 and distal grip 50 includes an enlarged convex configuration where the convexity of the respective grip extends orthogonally to the plane of the concavity of concave surfaces 58, 60. In addition, the lateral width of proximal grip 48 and distal grip 50 represent the widest portions of the illustrated form of surgical retractor 10. In one form, lateral width $lw_1$ of proximal grip 48 may be the same as lateral width $lw_2$ of distal grip 50, although forms in which lateral width $lw_1$ of proximal grip 48 is different from lateral width $lw_2$ of distal grip 50 are contemplated. In one form, lateral width $lw_1$ and lateral width $lw_2$ may be in the range of about 5 mm to about 12 mm. In another form, lateral width $lw_1$ and lateral width $lw_2$ may be in the range of about 6 mm to about 11 mm. In yet another form, lateral width $lw_1$ and lateral width $lw_2$ may be in the range of about 7 mm to about 10 mm, although other variations are contemplated.

Intermediate connecting portion 52 includes a first surface 62 positioned opposite of a second surface 64. With reference to FIG. 2 for example, it can be seen that first surface 62 includes a linear configuration that extends from concave surface 60 toward proximal end 14. At a location opposite of concave surface 58, first surface 62 transitions to an arcuate or curvilinear configuration and combines with surface 66 of proximal neck 54, positioned opposite of surface 68, to form a concave surface 70 which is positioned opposite of convex surface 72. Concave surface 70 is positioned on the same side of longitudinal axis L as concave surface 60. In addition, the concaveness of concave surface 70 is less than the concaveness of concave surface 60, although forms in which the concaveness of these surfaces is the same or opposite of the illustrated form are possible.

FIG. 2 also illustrates that second surface 64 of intermediate connecting portion 52 includes a linear configuration that extends from concave surface 58 toward distal end 16. At a location opposite of concave surface 60, second surface 64 transitions to an arcuate or curvilinear configuration and combines with surface 76 of distal neck 56, positioned opposite of surface 74, to form a concave surface 78 which is positioned opposite of convex surface 80. Concave surface 78 is positioned on the same side of longitudinal axis L as concave surface 58. In addition, the concaveness of concave surface 78 is less than the concaveness of concave surface 58, although forms in which the concaveness of these surfaces is the same or opposite of the illustrated form are possible.

With particular reference to FIG. 3 for example, proximal neck 54 tapers in width from proximal grip 48 toward proximal blade portion 18, although portion 54a of proximal neck 54 adjacent proximal blade portion 18 has a constant width which is less than that of proximal blade portion 18. Similarly, distal neck 56 tapers in width from distal grip 50 toward distal blade portion 20, although portion 56a of distal neck 56 adjacent distal blade portion 20 has a constant width which is less than that of distal blade portion 18.

Figure 6:
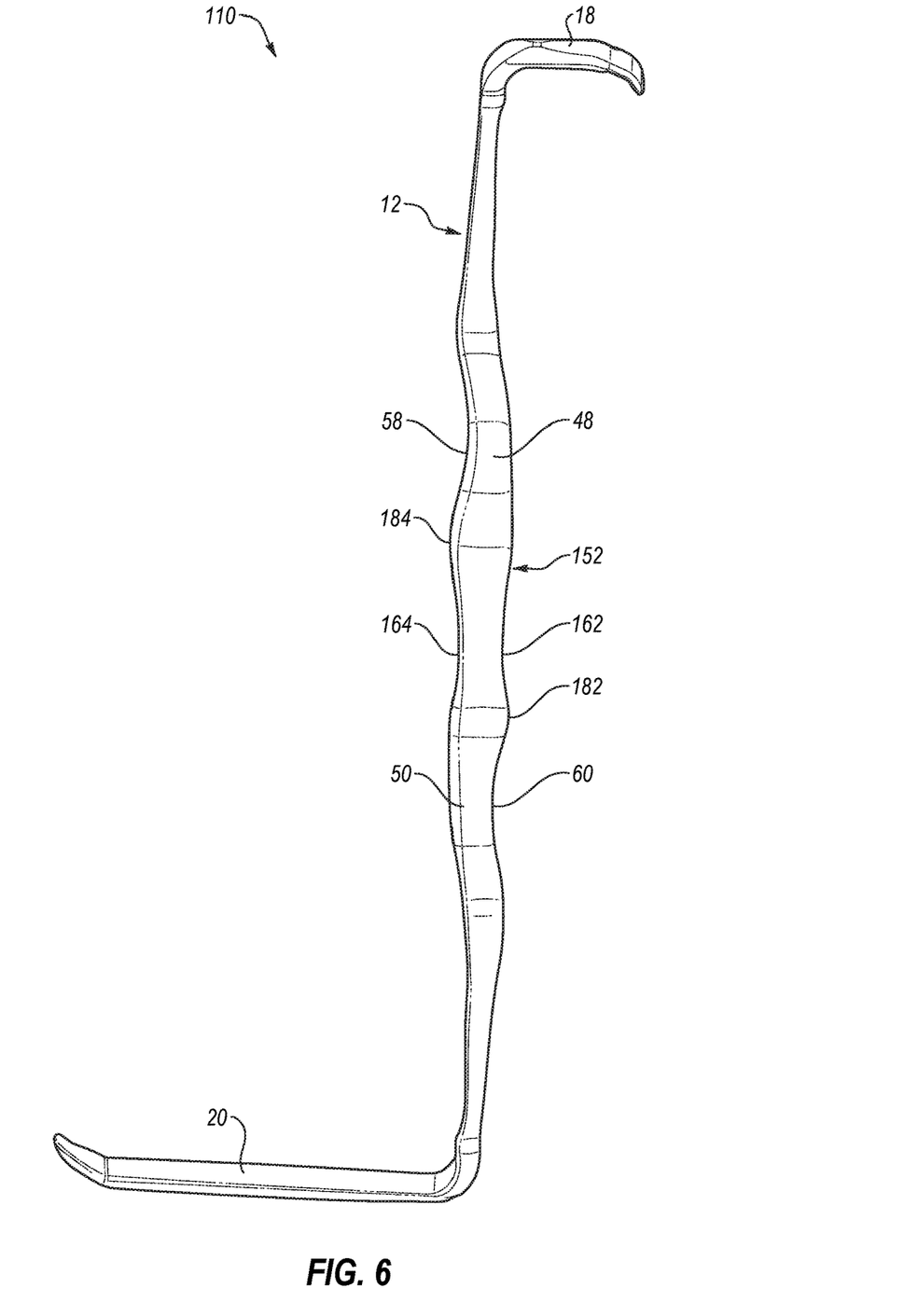
FIG. 6 is a side perspective view of an alternative embodiment surgical retractor.

An alternative embodiment surgical retractor 110 is illustrated in FIG. 6, where like numerals refer to like features previously described. Surgical retractor 110 is substantially similar to surgical retractor 10. However, in contrast to surgical retractor 10, surgical retractor 110 includes an intermediate connecting portion 152 which is positioned between and spaces apart proximal grip 48 and distal group 50 and includes a pair of oppositely positioned concave surfaces 162, 164. The presence of concave surface 60 in combination with concave surface 162 results in a projection or nob 182 while the presence of concave surface 58 in combination with concave surface 164 results in a projection or nob 184. The additional concave surfaces 162, 164 and the resulting nobs 182, 184 may assist, amongst other things, in the handling and manipulation of surgical retractor 110.

While not previously discussed, it should be appreciated that surgical retractors 10 and 110 may be formed of any suitable material or combination of materials. In one non-limiting form, surgical retractors 10 and 110 may be formed of surgical stainless steel, just to identify one exemplary material. Also, surgical retractors 10 and 110 may include one or more features in addition to those illustrated and previously described in this document. For example, one or more portions of surgical retractors 10 and 110 may include knurling or rubber gripping in order to assist with handling thereof.

It is contemplated that surgical retractors 10 and 110 may be suitable for use in any of a number of different surgical procedures. In one non-limiting form, a method includes use of surgical retractor 10 and 110 in a mini open carpal tunnel release surgical procedure.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A surgical retractor, comprising an elongate body extending along a longitudinal axis between a proximal end having a proximal blade portion extending transversely to the longitudinal axis and an opposite distal end having a distal blade portion extending transversely to the longitudinal axis, wherein:

the elongate body includes an intermediate connecting portion positioned between a first portion and a second portion, the first portion being positioned between the proximal and distal ends and having an enlarged lateral width, extending in a first direction relative to the longitudinal axis, relative to the intermediate connecting portion, and the second portion being positioned between the intermediate connecting portion and the distal end and having an enlarged lateral width, extending in the first direction, relative to the intermediate connecting portion;

the first portion includes a first concave surface positioned on a first side of the longitudinal axis, the first concave surface curving toward the longitudinal axis in a second direction extending transversely to the first direction;

the second portion includes a second concave surface positioned on an opposite, second side of the longitudinal axis relative to the first concave surface, the second concave surface curving toward the longitudinal axis in a third direction extending transversely to the first direction; and the intermediate connecting portion spaces the first concave surface from the second concave surface in a proximal-distal direction along the longitudinal axis in an arrangement where a proximal most portion of the second concave surface terminates distally of a distal most portion of the first concave surface.

2. The retractor of claim 1, wherein the first portion is spaced apart from the second portion.

3. The retractor of claim 2, wherein the first portion is spaced apart from the proximal end and the second portion is spaced apart from the distal end.

4. The retractor of claim 1, wherein the proximal blade portion and the distal blade portion extend substantially orthogonally to the longitudinal axis.

5. The retractor of claim 1, wherein the proximal blade portion extends from the elongate body in a first direction and the distal blade portion extends from the elongate body in an opposite, second direction.

6. The retractor of claim 1, wherein the concave surface positioned on the first portion is positioned on an opposite side of the longitudinal axis relative to the proximal blade portion.

7. The retractor of claim 6, wherein the concave surface positioned on the second portion is positioned on an opposite side of the longitudinal axis relative to the distal blade portion.

8. The retractor of claim 1, wherein the distal blade portion is longer than the proximal blade portion.

9. The retractor of claim 1, wherein the first portion has a maximum lateral width which is greater than a maximum lateral width of the proximal blade portion.

10. The retractor of claim 9, wherein the second portion has a maximum lateral width which is greater than a maximum lateral width of the proximal blade portion.

11. The retractor of claim 9, wherein the body includes a first connecting portion positioned between the first portion and the proximal blade portion, and the first connecting portion adjacent the proximal blade portion has a reduced width relative to the proximal blade portion.

12. The retractor of claim 11, wherein at least a portion of the first connecting portion tapers from the first portion toward the proximal blade portion.

13. The retractor of claim 12, wherein the intermediate connecting portion has a generally linear configuration, and the body further includes a second connecting portion positioned between the second portion and the distal blade portion.

14. The retractor of claim 13, wherein the second connecting portion adjacent the distal blade portion has a reduced width relative to the distal blade portion and at least a portion of the second connecting portion tapers from the second portion toward the distal blade portion.

15. The retractor of claim 1, wherein the intermediate connecting portion includes a first linear surface extending from the concave surface of the first portion and a second linear surface positioned opposite the first linear surface and extending from the concave surface of the second portion.

16. The retractor of claim 15, wherein the intermediate connecting portion includes a pair of oppositely positioned concave surfaces.

17. A surgical retractor, comprising an elongate body extending along a first axis between a proximal end with a proximal blade portion extending transversely to the first axis along a second axis in a first direction, and a distal end with a distal blade portion extending transversely to the first axis along the second axis in a second direction opposite of the first direction;

wherein the elongate body includes a proximal expanded portion, a distal expanded portion, and an intermediate connecting portion positioned between the proximal expanded portion and the distal expanded portion;

wherein the proximal expanded portion includes a concave portion positioned on a surface opposite of the proximal blade portion, the concave portion of the proximal expanded portion including an arc radius defined by a concentric point which is even with the first axis at a deepest central portion of the concave portion and is to the concave direction of the second axis;

wherein the distal expanded portion includes a concave portion positioned on a surface opposite of the distal blade portion, the concave portion of the distal expanded portion including an arc radius defined by a concentric point which is even with the first axis at a deepest central portion of the concave portion and is to the concave direction of the second axis;

wherein the intermediate connecting portion spans the proximal expanded portion to the distal expanded portion where a distal-most aspect of the concave portion of the proximal expanded portion defines a proximal portion of the intermediate connecting portion and a proximal-most aspect of the concave portion of the distal expanded portion defines a distal portion of the intermediate connecting portion; and wherein the proximal expanded portion has a maximum lateral width which is greater than a maximum lateral width of the proximal blade portion and the distal blade portion.

18. The retractor of claim 17, wherein the proximal expanded portion is spaced apart from the distal expanded portion.

19. The retractor of claim 18, wherein the proximal expanded portion is spaced apart from the proximal blade portion by a proximal connecting portion and the distal expanded portion is spaced apart from the distal blade portion by a distal connecting portion.

20. The retractor of claim 17, wherein the proximal blade portion and the distal blade portion extend substantially orthogonally along the second axis relative to the elongate body extending along the first axis.

21. The retractor of claim 17, wherein the concave portion of the proximal expanded portion is positioned on an opposite side of the first axis relative to the proximal blade portion.

22. The retractor of claim 21, wherein the concave portion of the distal expanded portion is positioned on an opposite side of the first axis relative to the distal blade portion.

23. The retractor of claim 17, wherein the distal blade portion is longer than the proximal blade portion.

24. The retractor of claim 17, wherein the distal expanded portion has a maximum lateral width which is greater than a maximum lateral width of the proximal blade portion and the distal blade portion.

25. The retractor of claim 17, wherein:

the elongate body includes a proximal connecting portion positioned between the proximal expanded portion and the proximal blade portion;

a proximal-most portion of the proximal connecting portion has a reduced width relative to the proximal blade portion;

the elongate body includes a distal connecting portion positioned between the distal expanded portion and the distal blade portion;

and a distal-most portion of the distal connecting portion has a reduced width relative to the distal blade portion.

26. The retractor of claim 25, wherein at least a portion of the proximal connecting portion and the distal connecting portion tapers from the proximal expanded portion and the distal expanded portion toward the proximal blade portion and the distal blade portion, respectively.

27. The retractor of claim 25, wherein at least a portion of the proximal blade portion and the distal blade portion tapers toward the proximal connecting portion and the distal connecting portion, respectively.

28. A surgical retractor, comprising an elongate body extending along a first axis between a proximal end with a proximal blade portion extending transversely to the first axis along a second axis in a first direction, and a distal end with a distal blade portion extending transversely to the first axis along the second axis in a second direction opposite of the first direction;

wherein the elongate body includes a proximal expanded portion, a distal expanded portion, and an intermediate connecting portion positioned between the proximal expanded portion and the distal expanded portion;

wherein the proximal expanded portion includes a concave portion positioned on a surface opposite of the proximal blade portion, the concave portion of the proximal expanded portion including an arc radius defined by a concentric point which is even with the first axis at a deepest central portion of the concave portion and is to the concave direction of the second axis;

wherein the distal expanded portion includes a concave portion positioned on a surface opposite of the distal blade portion, the concave portion of the distal expanded portion including an arc radius defined by a concentric point which is even with the first axis at a deepest central portion of the concave portion and is to the concave direction of the second axis;

wherein the intermediate connecting portion spans the proximal expanded portion to the distal expanded portion where a distal-most aspect of the concave portion of the proximal expanded portion defines a proximal portion of the intermediate connecting portion and a proximal-most aspect of the concave portion of the distal expanded portion defines a distal portion of the intermediate connecting portion; and wherein the intermediate connecting portion includes a first linear surface that extends proximally from a proximal-most aspect of the distal expanded portion to the proximal blade portion and a second linear surface that extends distally from a distal-most aspect of the proximal expanded portion to the distal blade portion.

29. The retractor of claim 28, wherein the intermediate connecting portion connects between the proximal expanded portion and the distal expanded portion.

30. The retractor of claim 29, wherein the concave portion of the proximal expanded portion is positioned on a first side of the first axis opposite the direction of the proximal blade portion.

31. The retractor of claim 30, wherein the concave portion of the distal expanded portion is positioned on a second side of the first axis opposite the direction of the distal blade portion.

* * * * *